(12) United States Patent
Bleeker et al.

(10) Patent No.: US 8,809,626 B2
(45) Date of Patent: Aug. 19, 2014

(54) TRICHOME SPECIFIC PROMOTERS

(75) Inventors: Petronella Martina Bleeker, Amsterdam (NL); Christianus Cornelis Nicolaas Van Schie, San Diego, CA (US); Paul Johan Diergaarde, Amersfoort (NL); Robert Cornelis Schuurink, Amsterdam (NL); Michel Albertus Haring, Haarlem (NL); Michiel Theodoor Jan De Both, Wageningen (NL)

(73) Assignee: KeyGene N.V., Wageningen (NL)

( * ) Notice: Subject to any disclaimer, the term of this patent is extended or adjusted under 35 U.S.C. 154(b) by 779 days.

(21) Appl. No.: 12/809,695

(22) PCT Filed: Dec. 16, 2008

(86) PCT No.: PCT/NL2008/050803
§ 371 (c)(1),
(2), (4) Date: Jan. 24, 2011

(87) PCT Pub. No.: WO2009/082208
PCT Pub. Date: Jul. 2, 2009

(65) Prior Publication Data
US 2011/0113512 A1    May 12, 2011

(30) Foreign Application Priority Data
Dec. 21, 2007 (EP) .................................. 07123967

(51) Int. Cl.
| C12N 15/82 | (2006.01) |
| C12N 5/04 | (2006.01) |
| C12N 5/14 | (2006.01) |
| C12N 15/00 | (2006.01) |
| C07H 21/04 | (2006.01) |
| A01H 5/00 | (2006.01) |

(52) U.S. Cl.
CPC .................................. C12N 15/8223 (2013.01)
USPC .......... 800/287; 800/298; 800/317; 536/24.1; 435/419; 435/320.1; 435/430; 435/468

(58) Field of Classification Search
None
See application file for complete search history.

(56) References Cited

U.S. PATENT DOCUMENTS

| 6,730,826 B2 | 5/2004 | Wagner et al. |
| 2003/0100050 A1 | 5/2003 | Wagner et al. |

FOREIGN PATENT DOCUMENTS

| EP | 1715050 A | 10/2006 |
| EP | 1715050 A1 | 10/2006 |
| JP | 6 303997 A | 11/1994 |
| WO | WO 02/04651 A2 | 1/2002 |
| WO | WO2004/111183 | * 12/2004 |
| WO | WO 2004/111183 A2 | 12/2004 |
| WO | WO2004111183 A | 12/2004 |

OTHER PUBLICATIONS

Shinozaki, Curr Opin Plant Biol 6:410-17 (2003).*
Wang et al., J. Exp. Botany 53:1891-97 (2002).*
Millar_Meth Mol Biol 34-425_2006.*
European Communication received in the related European Patent Application No. 08 863 616.2, dated Nov. 12, 2012.
Wang, E. et al.,"Isolation and characterization of the CYP71D16 trichome-specific promoter from *Nicotania tabacum* L," Journal of Experimental Botany, 2002, 53:1891-1897.
Wang, E. et al.,"Elucidation of the functions of genes central to diterpene metabolism in tobacco trichomes using posttranscriptional gene silencing," Planta, 2003, 216:686-691E.
Database EMBL,"POTEI55TF *Solanum tuberosum* RHPOTKEY BAC ends *Solanum tuberosum* genomic clone RHPOTKEY041_J13, genomic survey sequence," 2007, EBI accession No. EMBL:EI835693.
Database EMBL,"POTN327TF *Solanum tuberosum* RHPOTKEY BAC ends *Solanum tuberosum* genomic clone RHPOTKEY118_F06, genomic survey sequence," 2007, EBI accession No. EMBL:ER866105.
The Search Report received in the related European Patent Application No. EP 12190132.6, dated Dec. 3, 2012.
Databse EMBL [Online], Mueller, et al., "BAC end sequencing from three *Solanum lycopersicon* libraries", XP002687178, Aug. 12, 2005, Database accession No. CZ999395 *abstract*.
Wang, et al., "Isolation and characterization of the *CYP71D16* trichonne-specific promoter from *Nicotiana tabacum* L.", *Journal of Experimental Botany*, vol. 53, No. 376, pp. 1891-1897.
Office Action mailed Nov. 5, 2013 in Japan Patent Application No. 2010-539326, 11 pgs.
Van Schie et al., "Tomato linalool synthase is induced in trichomes by jasmonic acid," Plant Mol Biol., Apr. 12, 2007, vol. 64, pp. 251-263.

* cited by examiner

*Primary Examiner* — Brent T Page
*Assistant Examiner* — Russell Boggs
(74) *Attorney, Agent, or Firm* — Sunit Talapatra; Foley & Lardner LLP

(57) ABSTRACT

Trichome specific plant promoters are provided herein. Also provided are transgenic cells and organisms, especially plant cell and plants, comprising an trichome specific promoter and methods for expressing nucleic acid sequences in cells and organisms using trichome specific promoters.

13 Claims, 3 Drawing Sheets

SEQUENCE LISTING

<160> NUMBER OF SEQ ID NOS: 19

<210> SEQ ID NO 1
<211> LENGTH: 1426
<212> TYPE: DNA
<213> ORGANISM: Solanum habrochaites

<400> SEQUENCE: 1

```
tatctataga ccatatctag taggattttt gaagaagaga atgagtaatc aataataaat      60
aatgttttg aaattcaatt aaactaattt aaacaactca tgtgataatg taaggatcca     120
cataaattgg aggaggcggg ggggaggtat taaaaatgca cttgtggtta tacaaccaac     180
atccttaatt aggacaattt tgaaaaagca taaatatgtg gccagtaatt caacacataa     240
ggaagaggtg acatttattt cttttgcaaa acctactacc ttgttaccct tgctgtctct     300
tattacaccc ccagaacctt tagtcttggt attacaatca tatcatccaa cgatatttaa     360
tttccttttg tttatggtat gttttgattt tcagcagcaa taatgaaaag gggcggcaaa     420
ataggatgac cttgtttgat cccccaagtg gaagctaatt aaaaaaaaaa agcatgtcta     480
ataccaatta taatgattga ataccaaaca ttagagatag ttgtcacgct ccaaggctat     540
tcctagacgt aatagaagat ccaggatcac gagtgacttc aagctaacgc tgagtctagt     600
atatatcaag catgttgata agataactaa gataagcaca agcataaact aaaggactgc     660
aaatgaaaat atatttgaat atctagagga gacaattcca taacacttaa caccgactct     720
aactctaagt ttgaacttgc tactatgtgt gaaaaagcct ctaactgaaa tgagttttg     780
agatatgccc tcaagctaac tctaatgaaa ctgaaagtaa agactaaaac aaaaggcatg     840
tctagtgtct tcgaagtatg agggttcacc actagtgaaa tatcatatac ctaatgaatt     900
agatgaaatc tacggataaa ttctttggat ttcggggttg aacttcgaag aacacctcta     960
cttgttcttg aaaggaacta gcgacttctt cttttctttt cgctcaaagt tgggtgattt    1020
taagagaatg agggttttgg ataggttgtg actagattat taggtttaga ccagaaaaaa    1080
ctacatagtt ttgacattaa acgatgtagt ttaagtgtct aacgcacagg aaaaaagatc    1140
aaaacgaccc tgatgtagtt tataaacaag tcatcatgtt aagcacaaca ctacatgcaa    1200
tagtgtgaaa aaaattgcac ttttttaaag ataattatat gtaactaatt ctaattaata    1260
agcctagact tatagtgttt tcttaagcaa ccaataacaa attaattgat tcccaaaaaa    1320
ttcgattcaa agtagtaagg tacattataa ataggcccat cctattagca taacttaaac    1380
ccccaaatta agcttgaaaa aaaaaaaaaa aaacttagaa caagca                   1426
```

<210> SEQ ID NO 2
<211> LENGTH: 1907
<212> TYPE: DNA
<213> ORGANISM: Solanum lycopersicum

<400> SEQUENCE: 2

```
atatatatat atcataacta gtagaatttt gaaaaaagaa taattaacca ataataaata      60
atatttttga aatctgtcca attaattttg tttaaacaag tcatgtgatc atataagggt     120
ccacaaaaat tggaggtggt gatcagaaat gtacgagaaa gagttgtgtt tatacaatca     180
acatccttag aacaatgtta gagaaattgt aagtatggcc agtaattcaa catataaggc     240
```

```
aaaggtgaca tttatttctt ttccgaaacc tactaccttg ttaccgttat tctcctatta    300
cacctccaga acctttagtc ttggtatcat aatcatataa tccaacaata tttggttttta   360 cacctttgtt tagggtatgt tttaattttc agcagcaata atgaaaaggg acggggaaat    420
atgatcacct tgtttgagcc ctcgagtgga agtgaaaaaa acatttctag tacaattttat   480 aataaaggaa taccaaacat cagagatact tgtaatgcct cgaggatatc ccttggacgt    540
aataggagat ctaggatcac gagcgatccc aggtttctca agctaacttt gagcctgaca    600
tatatcaagc tataagacta agataagcag aagcatcact aataaattag tcaaaactaa    660
cggattccaa atgaaaatat atctgaatat ctagaggaaa tcaaacaatc ccaaaacact    720
taacactgcc tccaaatttg aatctactac tattcttaaa actctgtaac tgaaatgagt    780
tgttggaaca tgcccctaac taactctaac caaactgaaa acttaaagta aacactaaaa    840
taaaaggaat gtctattgtc cttgaagtat aagctcatca ttgaagctac tgaagttgaa    900
tcgagaatca atttaagcat gattggatat tgagtgtctg aacctgcatc atgaaacgat    960
gtagcacaaa gtatgcatca atacttagaa tgtactgagc atgcaggata tagatatgtt   1020
aagttgcaca agtatataa actgaataat ccataattga gcaatgatat aatctaaaca    1080
agggcataga tatgtattga agtatatcgc aaaactgaac tgaatgcaat tatcaagtac   1140
taatcatgaa gataacatgt tgaactgtat actgatgtaa atgttgaaaa cctggtcaat   1200
gcactaagag tctggttatg gggagctact attaatcgac ttaaaccacg tgagctaaac   1260
gtgaaatccg atgtatacgc ctcatcgaga gaattcaata acattccatg ggtataaaag   1320
catgattgtg gcgtgatcac taaaatctga tgcctaacag aggggactct gaacctatgt   1380
tggcacgtaa ttttaagact tgggggtat gctgaaactc ttgtccaact cgatgctaag    1440
tctacttcca acttgaatat tttttaagct aagatgtact taatactgaa tagctcaaaa   1500
gttgatatgc taactgaaag tgcaatattt atatactgag aatatagaat tcgaaatcga   1560
aagcatgaat ttatgtctgg ttagctaagc aagtataatt catgaactag ataatatata   1620
tgtgaaagta gttggtgttt tatcaccga gttttttgtt caaccatcta atctactctg    1680
catagccttt atttagatcg gatcggactc accttgttat tatgcaatag tgtaaaaaga   1740
tttgcacttt ttaaaagatt ttaaaattat atgtaagtaa ttctaataat aagctagcct   1800
agacttatag tgttgactta agcaaccaaa taacaaatta taaataggtc catcctatta   1860
gcataactta aacccacaaa ttaagcttga aaaaagcaa acaagca                  1907
```

<210> SEQ ID NO 3
<211> LENGTH: 1253
<212> TYPE: DNA
<213> ORGANISM: Solanum lycopersicum

<400> SEQUENCE: 3

```
gtttcattca aagtagtggt gtccaatacc aattatgtat tgctaatgaa tgtaacacgt     60
tgatgaatag tatccaatat attggaaagt catagtttga gttccaacat ctaaaagata    120
tattagttta aaacattata aaaggtgtga atcaacaaca caggaatggt gagggtgtgt    180
gtctctcaac tgctgccaaa attaaattag ctgaaccaaa tcccaatact acccgacgtt    240
cagggaatta aaaacctact acctgcaatt tcaatatttt tcactccatc gataataatt    300
acgtggtatg tatatatata atggttgaga tttaaaatct gtttggatct agttgtttta    360
ggcattttta tttaaataac atttaaatat ttttataata tcaattaaat attttttaaag   420
```

-continued

| | |
|---|---|
| ttaaaataaa ttaactagat tgcaaattgt cctattttc catattgaaa taatggttgc | 480 |
| gcaaggaagc gttgaaatat ttatgagttc acctgtattc agtgttgaaa tcgttgtaga | 540 |
| aagcaagtag gactctatag cattgtgact ttttttacca aaactaggtt cattaatttc | 600 |
| tactctaaca tcgaatttga gtcatggagt tacttgaatc aatcaacagt attaaatgtg | 660 |
| cttcatcaat attactaata aatactatca cctatagagg cattatcaaa catgtatgta | 720 |
| tatatgagaa gctttctagt acaacaattt tcttcgtaaa atttattcgc atcgggtatt | 780 |
| tatactaagt caatacatgc atatcatttg tttgaattta taatttattt tacttcatta | 840 |
| aatctagtaa taatgaaaat cgcatcgaat tggtataaac atccgatacg agtaagtgta | 900 |
| aacacatata cacatgcaaa aacagtggtg gagctataat ttggtccaag gggtgtataa | 960 |
| atataaagaa ataaaatcgt gtagaagtca aagactgtca gtacacccctt cactgtggct | 1020 |
| ccgccaccgt gcgcaaatat tttagcacat gtgctatttt tatgctacac atagtatatg | 1080 |
| tgctattttt atgctatatt tatactacac atactaggta ggtacatagt tgatttattt | 1140 |
| accattctat ccctaggaag tttctcttgt attactgata tacaatacaa aaaattttct | 1200 |
| ttatattctt tcatgtttaa catcttaaaa agtaattgag cagaacaaat aaa | 1253 |

<210> SEQ ID NO 4
<211> LENGTH: 44
<212> TYPE: DNA
<213> ORGANISM: Artificial sequence
<220> FEATURE:
<223> OTHER INFORMATION: adapter long strand

<400> SEQUENCE: 4
ctaatacgac tcactatagg actcgagcgg ccgcccgggc aggt    44

<210> SEQ ID NO 5
<211> LENGTH: 12
<212> TYPE: DNA
<213> ORGANISM: Artificial sequence
<220> FEATURE:
<223> OTHER INFORMATION: adapter short strand

<400> SEQUENCE: 5
acctgcccgg gc    12

<210> SEQ ID NO 6
<211> LENGTH: 22
<212> TYPE: DNA
<213> ORGANISM: Artificial sequence
<220> FEATURE:
<223> OTHER INFORMATION: adapter primer

<400> SEQUENCE: 6
ctaatacgac tcactatagg gc    22

<210> SEQ ID NO 7
<211> LENGTH: 22
<212> TYPE: DNA
<213> ORGANISM: Artificial sequence
<220> FEATURE:
<223> OTHER INFORMATION: nested adapter primer

<400> SEQUENCE: 7
tcgagcggcc gcccgggcag gt    22

<210> SEQ ID NO 8
<211> LENGTH: 27

```
<212> TYPE: DNA
<213> ORGANISM: Artificial sequence
<220> FEATURE:
<223> OTHER INFORMATION: ShSTS1 promoter (8)

<400> SEQUENCE: 8
ccccaaacag ttgggtgaaa attagcc                                        27

<210> SEQ ID NO 9
<211> LENGTH: 30
<212> TYPE: DNA
<213> ORGANISM: Artificial sequence
<220> FEATURE:
<223> OTHER INFORMATION: ShSTS1 nested (9)

<400> SEQUENCE: 9
ggacgagact tattagcaga agaagcagcc                                     30

<210> SEQ ID NO 10
<211> LENGTH: 30
<212> TYPE: DNA
<213> ORGANISM: Artificial sequence
<220> FEATURE:
<223> OTHER INFORMATION: SlSTS1 promoter (43)

<400> SEQUENCE: 10
ttcatgagta taagaaagga aatgatatcc                                     30

<210> SEQ ID NO 11
<211> LENGTH: 28
<212> TYPE: DNA
<213> ORGANISM: Artificial sequence
<220> FEATURE:
<223> OTHER INFORMATION: SlSTS1 nested (44)

<400> SEQUENCE: 11
ggaaatgata tccccaaaca gatgggtg                                       28

<210> SEQ ID NO 12
<211> LENGTH: 26
<212> TYPE: DNA
<213> ORGANISM: Artificial sequence
<220> FEATURE:
<223> OTHER INFORMATION: SlMTS1 promoter (54)

<400> SEQUENCE: 12
ggtaaataat gatggtctct tgaagg                                         26

<210> SEQ ID NO 13
<211> LENGTH: 25
<212> TYPE: DNA
<213> ORGANISM: Artificial sequence
<220> FEATURE:
<223> OTHER INFORMATION: SlMTS1 nested (55)

<400> SEQUENCE: 13
gaccaccatc atccctatgt tactc                                          25

<210> SEQ ID NO 14
<211> LENGTH: 25
<212> TYPE: DNA
<213> ORGANISM: Artificial sequence
<220> FEATURE:
<223> OTHER INFORMATION: ShSTS1 full forward

<400> SEQUENCE: 14
```

```
ccctcgagta tctatagacc atatc                                          25

<210> SEQ ID NO 15
<211> LENGTH: 26
<212> TYPE: DNA
<213> ORGANISM: Artificial sequence
<220> FEATURE:
<223> OTHER INFORMATION: ShSTS1 full reverse

<400> SEQUENCE: 15
gcagaagaag cagccatggc ttgttc                                         26

<210> SEQ ID NO 16
<211> LENGTH: 36
<212> TYPE: DNA
<213> ORGANISM: Artificial sequence
<220> FEATURE:
<223> OTHER INFORMATION: SlSTS1 full forward

<400> SEQUENCE: 16
ttaattaagc atatatatat atatcataac tagtag                              36

<210> SEQ ID NO 17
<211> LENGTH: 31
<212> TYPE: DNA
<213> ORGANISM: Artificial sequence
<220> FEATURE:
<223> OTHER INFORMATION: SlSTS1 full reverse

<400> SEQUENCE: 17
gcggccgctg cttgtttgct tttttcaag c                                    31

<210> SEQ ID NO 18
<211> LENGTH: 31
<212> TYPE: DNA
<213> ORGANISM: Artificial sequence
<220> FEATURE:
<223> OTHER INFORMATION: SlMTS1 full forward

<400> SEQUENCE: 18
gcggccgcgt ttcattcaaa gtagtggtgt c                                   31

<210> SEQ ID NO 19
<211> LENGTH: 28
<212> TYPE: DNA
<213> ORGANISM: Artificial sequence
<220> FEATURE:
<223> OTHER INFORMATION: SlMTS1 full reverse

<400> SEQUENCE: 19
ccatggttta tttgttctgc tcaattac                                       28
```

TRICHOME SPECIFIC PROMOTERS

FIELD OF THE INVENTION

Figure 1:
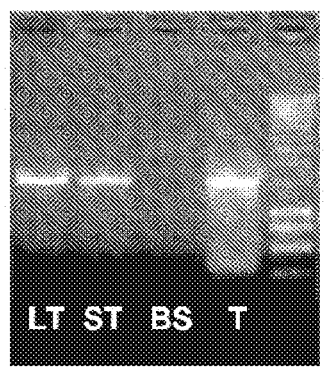

The present invention relates to trichome specific plant promoters and their uses. The promoters may be used for expression of homologous or heterologous proteins in trichome cells, or for the expression of active nucleic acid molecules, such as sense and/or anti-sense RNA. Provided are nucleic acid sequences having promoter activity, as well as chimeric genes, vectors and recombinant (transgenic) cells and organism comprising these. Also provided are methods for making transgenic cells and organisms, especially plants and plant cells, comprising the promoters. The promoters are useful for the production of various compounds in trichomes, such as pesticides, volatile oils, flavours or fragrances, pharmaceutical components, cytotoxic proteins and the like.

BACKGROUND OF THE INVENTION

Trichomes are various outgrowths of the epidermis in plants including branched and unbranched hairs, vesicles, hooks spines and stinging hairs. Trichomes are staked, multicellular protruding structures that are considered important in the protection of plants against herbivores, but also against water loss by transpiration and UV irradiation (Mauricio & Rausher, 1997, Evolution 51, 1435 Wagner et al. 2004, Ann Bot 93, 3), as sinks for toxic heavy metals and xenobiotics (Salt et al., 1995, Plant Phys 109, 1427; Domínguez-Solis et al. 2001, J Biol Chem 276, 9297; Gutiérrez-Alcalá et al. 2000, PNAS 97, 11108).

Glandular trichomes containing various secondary compounds are present on the foliage of many solanaceous species and their role in resistance to various pests has been well documented (e.g. Juvik et al. 1988, J Chem Ecol 14, 1261; Heinz & Zalom, 1995, J Econ Entomol 88, 1494; Kennedy & Sorenson, 1985, J Econ Entomol 78, 547; Gurr, 1995, Plant Prot Quart 10,17; Gurr & McGrath, 2002, Ann App Biol Cabo et al., 2006, J Exp Bot 57, 3911) Glandular trichomes in tomato contain high amounts of terpenes (van der Hoeven et al., 2000) and methylketones (Fridman et al., 2005). Trichomes have been categorised into types I to VII (Luckwill, 1943, Aberdeen University Press, UK) with types I, IV, VI and VII as glandular trichome types and II, III, and V as non-glandular. Type IV, V and VI are the prevalent trichomes on the wild tomato *S. habrochaites* (Simmons and Gurr, 2005, Agricultural and Forest Entomol 7, 265). In *S. pennelli* resistance to pests is predominantly related to the chemistry and density of type IV glandular trichomes, which cover all parts of the plant (Simmons et al., 2003 Aus J Entomol 43, 196; 2004, Entomol Exp App 113, 95). When exudates of glandular trichomes are physically removed, pest survival and longevity increases while mortality and entrapment decreases (Simmons and Gurr, 2005, Agricultural and Forest Entomol 7, 265). Trichome types IV and VI have been positively correlated with pest control.

Non-glandular trichomes of cotton ovules have been explored as targets for biotechnology with high economic importance (Kim and Triplett, 2001, Plant Physiol 127, 1361). The ability of glandular trichomes to secrete various phytochemicals, such as acyl sugars in *S. pennelli* and methyl ketones and terpenes in *S. habrochaites*, makes these structures potentially suitable for biotechnological application and provides opportunities for trichome based pest management.

Protein expression in trichomes can be utilised for the production of useful compounds such as pesticides, pharmaceutical components, volatile oils, flavours and fragrances (Callow, 2000 Advances in botanical research eds. Hallahan and Gray, San Diego Academic Press; Wagner 2004 Ann Bot 93, 3). In order to generate components specifically in trichomes, regulation of gene expression in the plant trichome is necessary. The possibility to direct protein expression in specialised structures or cells avoids interference in the plants metabolic pathways and consequently the plants' performance.

Constitutive strong promoters such as the well known Cauliflower Mosaic Virus promoter (CaMV 35S) promoter are generally used in ectopic-expression studies. However this type of promoter is not very suitable for the expression of specific and possibly phytotoxic compounds, such as terpenes. Moreover, exhaustion of metabolic pools might be problematic.

Gutierrez-Alcala (2005, J Exp Bot 56, 2487) describes the promoter of the *Arabidopsis thaliana* OASA1 gene, which has activity in both glandular and non-glandular trichomes of tobacco.

Wang et al. (2002, J Exp Bot 53, 1891) describes a trichome specific promoter from tobacco P450 gene, CYP71D16, which shows expression in tobacco glandular trichomes at all developmental stages.

WO2004/111183 describes trichome specific promoters from tomato and tobacco leaves. However, upon testing transgenics described in WO2004/111183 no satisfactory results were obtained in the sense that expression was not trichome specific (e.g. additional expression in leaf veins) and expression was weak.

Despite trichome specific promoters having been isolated, a need for different trichome specific or trichome preferred promoters remains. The present invention provides trichome specific transcription regulatory sequences which are suitable for directing expression of operably linked nucleic acid molecules in trichomes, especially in glandular trichomes found on various plant surfaces (aerial parts such as leaves, stems, floral organs) while, in some species, they are absent from particular plant surfaces such as the fruit and seeds. Simple trichomes are present on aerial surfaces of most angiosperms and some gymnosperms and bryophytes (Wagner et al. 2004, Ann Bot 93, 3). In angiosperms trichomes may occur on leaves, petals, petioles, peduncles, stems and seed coats, depending on the species. Glandular trichomes are found on perhaps 30% of vascular plants (Dell and McComb, 1978, Adv Bot Res 6, 227; Fahn, 2000, Adv Bot Res 31, 37).

SUMMARY OF THE INVENTION

Provided is a transgenic plant or plant cell or plant tissue or organ comprising a chimeric gene integrated in its genome, characterized in that said chimeric gene comprises a trichome specific promoter operably linked to a homologous or heterologous nucleic acid sequence, wherein the promoter is selected from the group of:
  (a) the nucleic acid sequence of SEQ ID NO: 1, SEQ ID NO: 2 or SEQ ID NO: 3 (or its complement),
  (b) a functional fragment of SEQ ID NO: 1, SEQ ID NO: 2 or SEQ ID NO: 3 (or its complement);
  (c) a nucleic acid sequence comprising at least 70% sequence identity with SEQ ID NO: 1 or SEQ ID NO: 2 or SEQ ID NO: 3 (or its complement);
  (d) a functional fragment of the nucleic acid sequence of (c) comprising transcription regulatory activity.

Also provided is an isolated nucleic acid sequence having promoter activity when introduced into plant cells, wherein said nucleic acid sequence comprising a sequence selected from:

(a) the nucleic acid sequence of SEQ ID NO: 1, SEQ ID NO: 2 or SEQ ID NO: 3 (or its complement),
(b) a functional fragment of SEQ ID NO: 1, SEQ ID NO: 2 or SEQ ID NO: 3 (or its complement);
(c) a nucleic acid sequence comprising at least 70% sequence identity with SEQ ID NO: 1 or SEQ ID NO: 2 or SEQ ID NO: 3 (or its complement);
(d) a functional fragment of the nucleic acid sequence of (c) comprising transcription regulatory activity.

Vectors, chimeric genes and host cells comprising the above sequences are also an embodiment of the invention.

Further, a method is provided for making a transgenic plant or plant cell, comprising the steps of:
(a) generating a chimeric gene comprising a promoter as described above, operably linked to a nucleic acid sequence to be transcribed, and optionally further linked to a 3'UTR nucleic acid sequence, or a vector comprising such a chimeric gene;
(b) transforming a plant or plant cell with said chimeric gene or vector; and, optionally,
(c) regenerating transgenic plants or plant cells.

The method may further comprise growing the transgenic plant (or a derivative thereof, such as derived from crossing or selfing and wherein the derivative retains the chimeric gene) and harvesting the trichomes or parts thereof (trichome exudates) for further use (molecular farming).

Alternatively, for example if the chimeric gene increases pest and/or pathogen resistance of the plant, the method may further comprise growing the transgenic plant (or a derivative thereof, such as derived from crossing or selfing and wherein the derivative retains the chimeric gene) and harvesting all or part of the plant, such as the leaves, fruit, seeds, etc. for further use.

The promoter sequences provided here exhibit a clear and glandular-trichome specific expression. Additionally, it is shown here that the promoter sequence from a wild tomato is active in the trichomes of a cultivated tomato.

GENERAL DEFINITIONS

"Trichome" encompasses herein different types of trichomes, both glandular trichomes and/or non-glandular trichomes.

"Trichome cells" refers to the cells making up the trichome structure, such as the gland, or secretory cells, base cells and stalk, or stipe cells, extra-cellular cavity and cuticle cells. Trichomes can also consist of one single cell.

"Molecular farming" refers herein to the production and/or recovery of useful compounds from trichomes of transgenic plants expressing one or more chimeric genes in trichomes, whereby for example secondary metabolites, pharmaceutical compounds, fragrances or flavours are produced in the trichomes.

The term "nucleic acid sequence" (or nucleic acid molecule) refers to a DNA or RNA molecule in single or double stranded form, particularly a DNA having promoter activity according to the invention or a DNA encoding a protein or protein fragment.

An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein".

An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA) in a cell, operably linked to suitable transcription regulatory regions (e.g. a promoter). A gene may thus comprise several operably linked sequences, such as a promoter, a 5' non-translated leader sequence (also referred to as 5'UTR, which corresponds to the transcribed mRNA sequence upstream of the translation start codon) comprising e.g. sequences involved in translation initiation, a (protein) coding region (cDNA or genomic DNA) and a 3'non-translated sequence (also referred to as 3' untranslated region, or 3'UTR) comprising e.g. transcription termination sites and polyadenylation site (such as e.g. AAUAAA or variants thereof).

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more sense sequences (e.g. coding sequences) or to an antisense (reverse complement of the sense strand) or inverted repeat sequence (sense and antisense, whereby the RNA transcript forms double stranded RNA upon transcription).

A "3' UTR" or "3' non-translated sequence" (also often referred to as 3' untranslated region, or 3'end) refers to the nucleic acid sequence found downstream of the coding sequence of a gene, which comprises, for example, a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi, or silencing through miRNAs). An active protein in certain embodiments refers to a protein having a dominant-negative function due to a repressor domain being present. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. Down-regulation of gene expression can also take place through the action of microRNAs (miRNA), endogenous 21-24 nucleotide small RNAs processed from stem-loop RNA precursors (pre-miRNAs), Incorporated into a RNA-induced silencing complex (RISC), miRNAs down-regulate gene expression by mRNA cleavage or translational repression.

"Ectopic expression" refers to expression in a tissue in which the gene is normally not expressed.

A "transcription regulatory sequence" is herein defined as a nucleic acid sequence that is capable of regulating the rate of transcription of a nucleic acid sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers, but also silencers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream (5') with respect to the direction of transcription of the transcription initiation site of the gene (the transcription start is referred to as position +1 of the sequence and any upstream nucleotides relative thereto are referred to using negative numbers), and is structurally identified by the presence of a binding site for DNA-dependent RNA polymerase, transcription initiation sites and any other DNA domains (cis acting sequences), including, but not limited to transcription factor binding sites, repressor and activator protein binding sites, and any other sequences of nucleotides known to one of skill in the art to act directly or indirectly to regulate the amount of transcription from the promoter. Examples of eukaryotic cis acting sequences upstream of the transcription start (+1) include the TATA box (commonly at approximately position −20 to −30 of the transcription start), the CAAT box (commonly at approximately position −75 relative to the transcription start), 5'enhancer or silencer elements, etc.

A "constitutive" promoter (such as the CaMV 35S promoter) is a promoter that is active in essentially all tissues and organs under most physiological and/or developmental conditions. More preferably, a constitutive promoter is active under essentially all physiological and developmental conditions in all major organs, such as at least the leaves, stems, roots, seeds, fruits and flowers. Most preferably, the promoter is active in all organs under most (preferably all) physiological and developmental conditions.

However, a tissue-specific or tissue-preferred promoter (such as the promoters according to the invention) can also be referred to as being "constitutively active". The promoter is thus active under most developmental and/or physiological conditions, albeit in only a specific tissue or mainly in a specific tissue. A "promoter which has constitutive activity" or which is "constitutive" in a plant or plant cell refers, therefore, to a nucleic acid sequence which confers transcription in the plant or plant cells in the specific tissue under most physiological and developmental conditions.

An "inducible" promoter is a promoter that is physiologically (e.g. by external application of certain compounds) or developmentally regulated.

A "tissue specific" promoter is only active in specific types of tissues or cells, such as trichome cells. The promoter activity can therefore be described by referring to the circumstances under which the promoter confers transcription of the nucleic acid sequence operably linked downstream (3') of the promoter.

A "tissue preferred" promoter is preferentially, but not exclusively, active in certain tissues or cells, such as for example in trichome cells and epidermis cells.

A promoter which is "insensitive to one or more biotic and/or abiotic stresses" or whose activity "is not reduced when exposed to one or more biotic and/or abiotic stress conditions" refers to a nucleic acid sequence having promoter activity under normal physiological and developmental conditions, and whereby the activity is not, or at least not significantly, reduced quantitatively when biotic and/or abiotic stress is exerted on the organism (e.g. plant) or cells or tissues or organs comprising the promoter.

"Stress" refers to conditions or pressures of physical, chemical or biological origin acting on a plant or plant cells which may result in yield loss and/or quality loss of a plant, but which is not lethal to the plant. "Non-stress conditions" refer herein to conditions under which physiology and development are normal or optimal. "Biotic stress" refers to stress caused by biotic (live) agents, such as fungi, viruses, mycoplasma like organisms, insects, arthropods, bacteria, nematodes etc. (i.e. especially plant pests and pathogens). "Abiotic stress" refers to stress caused by abiotic (non-living) agents, such as temperature stress (cold/freezing, heat), salinity (salt), wind, metals, day-length (photoperiod), water-stress (such as too little or too much water availability, i.e. drought, dehydration, water-logging, etc.), etc.

As used herein, the term "operably linked" refers to a linkage of polynucleotide elements in a functional relationship. A nucleic acid is "operably linked" when it is placed into a functional relationship with another nucleic acid sequence. For instance, a promoter, or a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which are joined to form a functional protein, which displays the functionality of the joined domains (for example a DNA binding domain or a repression of function domain leading to a dominant negative function). A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain.

The term "target peptide" refers to amino acid sequences which target a protein to intracellular organelles such as plastids, preferably chloroplasts, mitochondria, or to the extracellular space (secretion signal peptide). A nucleic acid sequence encoding a target peptide may be fused (in frame) to the nucleic acid sequence encoding the amino terminal end (N-terminal end) of the protein. For example, target peptides for trichome cells include peptides which target leucoplasts, chloroplasts, mitochondria, nuclei, peroxisomes, endoplasmatic reticulum, plastids, extra-cellular cavities or vacuoles of the trichome cells.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US2002138879 and WO 95/06722), a co-integrate vector or a T-DNA vector, as known in the art and as described elsewhere herein, into which a chimeric gene is integrated or, if a suitable transcription regulatory sequence/promoter is already present, only a desired nucleic acid sequence (e.g. a coding sequence, an antisense or an inverted repeat sequence) is integrated downstream of the transcription regulatory sequence/promoter. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism), arising as a result of the introduction into said cell of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family. The host cell is preferably a plant cell, but may also be a bacterial cell, a fungal cell (including a yeast cell), etc. The host cell may contain the nucleic acid construct as an extra-chromosomally (episomal) replicating molecule, or more preferably, comprises the chimeric gene integrated in the nuclear or plastid genome of the host cell.

The term "selectable marker" is a term familiar to one of ordinary skill in the art and is used herein to describe any genetic entity which, when expressed, can be used to select for a cell or cells containing the selectable marker. Selectable marker gene products confer, for example, antibiotic resistance, or more preferably, herbicide resistance or another selectable trait such as a phenotypic trait (e.g. a change in pigmentation) or a nutritional requirement. The term "reporter" is mainly used to refer to visible markers, such as green fluorescent protein (GFP), eGFP, luciferase, GUS and the like, as well as nptII markers and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of a gene from one plant species may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. The stringency of the hybridization conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt (NaCl) concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"High stringency" conditions can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1× SSC, 0.1% SDS.

"Moderate stringency" refers to conditions equivalent to hybridization in the above described solution but at about 60-62° C. In that case the final wash is performed at the hybridization temperature in 1×SSC, 0.1% SDS.

"Low stringency" refers to conditions equivalent to hybridization in the above described solution at about 50-52° C. In that case, the final wash is performed at the hybridization temperature in 2×SSC, 0.1% SDS. See also Sambrook et al. (1989) and Sambrook and Russell (2001).

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as using the Smith Waterman algorithm, are preferred. Alternatively percentage similarity or identity may be determined by searching against public databases, using algorithms such as FASTA, BLAST, etc.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

Whenever reference to a "plant" or "plants" (or a plurality of plants) according to the invention is made, it is understood that also plant parts (cells, tissues or organs, seeds, severed or harvested parts, leaves, seedlings, flowers, pollen, fruit, stems, roots, callus, protoplasts, etc), progeny or clonal propagations of the plants which retain the distinguishing characteristics of the parents (e.g. presence of a trans-gene), such as seed obtained by selfing or crossing, e.g. hybrid seed (obtained by crossing two inbred parental lines), hybrid plants and plant parts derived therefrom are encompassed herein, unless otherwise indicated.

DETAILED DESCRIPTION

A constitutive promoter such as CaMV 35S promoter (single 35S promoter, described by Franck et al., 1980, Cell 21, 285-294) is not considered useful for the expression of genes which need to be regulated at a specific tissue level or under specific conditions only.

In the present invention several plant promoters are provided which exhibit a constitutive, but tissue specific activity in trichomes, and are optionally essentially insensitive to one or more biotic and/or abiotic stresses. Such promoters are desired for the controlled expression of nucleic acid sequences in transgenic plants.

In one embodiment the invention provides promoter regions of tomato genes (tomato terpene synthases and orthologs and homologs thereof) which confer constitutive, glandular trichome specific and/or glandular trichome preferred expression in host plants, such as cultivated tomato (*Solanum lycopersicum*), other Solanaceae and other plant families and species.

Nucleic Acid Sequences, Chimeric Genes and Vectors

In one embodiment isolated nucleic acid sequences (preferably genomic or synthetic DNA sequences), having promoter activity in plant cells, are provided which show strong, constitutive transcriptional trichome specific activity in plant trichomes, such as in trichomes found on leaves, stems and flower organs. Preferably, the promoters are active in one or more glandular (types I, IV, VI and/or VII).

Preferably the promoter activity of the nucleic acid sequences according to the invention is not reduced, or at least not significantly reduced, when the transgenic plant, or plant tissue or organ, is subjected to one or more abiotic and/or biotic stresses. A significant reduction in this respect refers to a statistically significant (quantitative) reduction of promoter activity by 1% or more (e.g. 2%, 3%, 5%, 10%, etc., up to 100%) compared to the activity in the same tissues or organs under non-stress conditions. Thus, preferably the promoters remain strong and constitutive (in trichome cells) under one or more stress conditions.

In one embodiment a trichome specific promoter is provided comprising or consisting of SEQ ID NO: 1, SEQ ID NO: 2, or SEQ ID NO: 3, or a nucleotide sequence essentially similar thereto (referred to as "variants", see definition below), or active (functional) fragments of any of these which have promoter activity in one or more trichome types and/or trichome cells, such as fragments of at least 200, 300, 400, 500, 600, 800, 900, 1000, 1200, 1500, 2000, 2400 or more consecutive nucleotides of SEQ ID NO: 1, 2 or 3, or of variants thereof.

"Active fragments" or "functional fragments", or "fragments having promoter activity" refer to nucleic acid fragments which are capable of conferring transcription in one or more trichome types and/or one or more trichome cells found on one or more different types of plant tissues and organs (e.g. on stems, leaves, flower buds or flower parts). Preferably active fragments confer trichome specific and/or at least trichome preferred expression, and they preferably have at least a similar strength (or higher strength) as the promoter of SEQ ID NO: 1, 2 or 3. This can be tested as described below, by transforming a plant with such a fragment, preferably operably linked to a reporter gene, and assaying the promoter activity qualitatively (spatio-temporal transcription) and/or preferably quantitatively in trichomes. Obviously, DNA fragments may be generated in a number of ways, e.g. using de novo DNA synthesis, or restriction enzymes, or terminal nucleases, etc. Deletion analysis, whereby fragments are generated which comprise 5' deletions of various sizes can for example be used to create stronger and/or more specific transcriptional activity.

In one embodiment, the strength of the promoter fragments is quantitatively essentially identical to, or higher than, that of the 35S promoter The promoters comprising or consisting of SEQ ID NO: 1, 2 or 3, variants thereof or functional fragments of any of these, are preferably insensitive to at least one (but preferably more, most preferably any) biotic and/or abiotic stress/es to which the plant or plant cell(s), tissues or organs comprising the promoter may be exposed (see below). Thus, activity remains constitutive and strong in the trichomes during exposure to one or more stress conditions.

Also provided are "variants" of the above trichome specific promoters, and functional fragments of such variants. These variants include nucleic acid sequences essentially similar to SEQ ID NO: 1 and/or SEQ ID NO: 2 and/or SEQ ID NO: 3 (and functional fragments of these variant sequences, as described above), and which have promoter activity, i.e. which are also capable of providing (preferably constitutive) transcription in plant trichomes. Sequences which are "essentially similar" to SEQ ID NO: 1 and/or 2 and/or 3 are nucleic acid sequences comprising at least about 50, 55, 60, 65, 70, 75, 80, 85, 90, 95, 96, 97, 98, 99% or more nucleic acid sequence identity to SEQ ID NO: 1 and/or to SEQ ID NO: 2 and/or SEQ ID NO: 3, using the Needleman and Wunsch or the Smith Waterman Pairwise alignment (e.g. program "needle" or "water" in Embosswin, e.g. version 2.10.0, with default gap creation and gap extension penalties) and which are trichome specific in their activity. In a preferred embodiment, the activity of the variants (and functional fragments) is strong in trichomes, i.e. quantitatively at least as strong (or stronger) than the activity provided by SEQ ID NO: 1, 2 or 3. Also the cell type specificity is at least as the specificity of SEQ ID NO: 1, 2 or 3 or more specific. In a further embodiment the activity of these variants (and functional fragments thereof) is insensitive to one or more biotic and/or abiotic stresses.

It is clear that many methods can be used to identify, synthesise or isolate variants or functional fragments of the nucleic acid sequences provided herein, such as nucleic acid hybridization, PCR technology, in silico analysis and nucleic acid synthesis, and the like. For example, nucleic acid hybridization can be used to identify DNA sequences in other plant species or varieties which hybridize to SEQ ID NO: 1, 2 or 3, or to fragments of these, under stringent or moderately stringent hybridization conditions.

Alternatively, sequence databases can be screened in silico for variant sequences using known algorithms, such as BLAST, FASTA, etc. In this way it is feasible to isolate variant sequences from other plant species or other varieties of tomato. Especially included herein are the promoters of other alleles of the same genes (monoterpene synthase 1, e.g. linalool synthase; sesquiterpene synthase 1) found in other varieties of tomato or in other plant species, especially species of the genus *Solanum*, as will be described below. For example, cDNA libraries may be constructed from one or more plant species, one or more varieties, or different tissues of one species or variety. The cDNA libraries may be screened for monoterpene synthase 1 or sesquiterpene synthase 1 cDNAs (using e.g. probes or primers derived from SEQ ID NO: 1, 2, 3, or fragments or variants thereof). Equally, differential display methods (such as cDNA-AFLP) may be used to identify such transcripts. Methods such as TAIL-PCR (Liu et al. 1995, Genomics 25(3):674-81; Liu et al. 2005, Methods Mol Biol. 286:341-8), Linker-PCR, or Inverse PCR (IPCR) may be used to isolate the upstream transcription regulatory region of the gene.

Variants of the same genes, i.e. orthologs and/or homologs of monoterpene synthase 1 (linalool synthase) and sesquiterpene synthase 1 include for example nucleic acid sequences (DNA or RNA) or amino acid sequences comprising at least 50, 55, 60, 65, 70, 75, 80, 85, 90, 95, 96, 97, 98, 99% or more nucleic acid or amino acid sequence identity to the nucleotide sequence or amino acid sequence of GenBank Accession numbers AY840091 (*S. lycopersicum* MTS1 cDNA and protein; van Schie et al. 2007, Plant Mol Biol. 64: 251-263), AF279455 (*S. habrochaites* SSTLH1; van der Hoeven et al. 2000, Plant Cell 12: 2283-2294 cDNA and protein), AF279453 (*S. lycopersicum* SSTLE1; van der Hoeven et al. 2000, Plant Cell 12: 2283-2294). Preferably sequence identity is determined by pairwise alignment using the Needleman and Wunsch or the Smith Waterman Pairwise alignment (e.g. program "needle" or "water" in Embosswin, e.g. version 2.10.0, with default gap creation and gap extension penalties). The promoters of these variants are preferably also trichome specific in their activity. Methods such as cDNA-AFLP, other PCR based methods or Northern hybridization may be used to isolate or identify such genes. Their promoter can be cloned using known methods. In a preferred embodiment, the promoter is obtained from a monoterpene synthase 1 (linalool synthase) and sesquiterpene synthase 1 gene from a plant belonging to the family Solanaceae, such as species of the genus *Solanum* (including the reclassified *Lycopersicon* species), *Nicotiana*, *Capsicum*, *Petunia*, *Coffea*, etc. Especially orthologs from wild species are desired.

Whether a nucleic acid sequence (or fragment of variant) has constitutive promoter activity, i.e. is capable of conferring transcription specifically in trichomes, whether the activity is "strong", and whether the activity of the nucleic acid sequence is insensitive to at least one (but preferably more, most preferably any) biotic and/or abiotic stress to which the transgenic cell, tissue, organ or organisms (especially plant or plant cell), may be exposed, can be determined using various methods. Generally, one can distinguish qualitative methods and quantitative methods. Qualitative methods (such as histological GUS staining) are used to determine the spatio-temporal activity of the promoter (is the promoter active or not in a certain tissue or organ, or under certain environmental/developmental conditions), while quantitative methods (such as fluorometric GUS assays) also quantify the level of activity, compared to controls. Suitable controls are, for example, plants transformed with empty vectors (negative control) or transformed with constructs comprising other promoters, such as the *Arabidopsis* CER6 promoter (Hooker et al. 2002, Plant Phys 129, 1568) which is active in the epidermis and trichomes of *N. tabacum*, or non-transgenic *Arabidopsis* plants.

To test and optionally quantify the relative or absolute activity, a cloned or synthetic nucleic acid molecule, such as SEQ ID NO: 1, 2 or 3, or variants thereof, or fragments of any of these, may be operably linked to a known nucleic acid sequence (e.g. a reporter gene, such as gusA, or any gene encoding a specific protein) and may be used to transform a plant cell using known methods and regenerate a plant therefrom.

The activity of the promoter can, for example, be assayed (and optionally quantified) by detecting the level of RNA transcripts of the downstream nucleic acid sequence, especially in the trichome cells. This may be done using quantitative methods, such as e.g. quantitative RT-PCR or other PCR based methods, and the like. Alternatively, the reporter protein or the activity of the reporter protein may be assayed and quantified. For example, if the reporter gene is the gus gene, a fluorometric GUS assay may be used, as described in the Examples. In this way, the quantitative promoter activity levels of transformed plants or plant cells maintained under normal physiological (non-stress) conditions can be compared to levels of plants or plant cells which are exposed to one or more biotic or abiotic stresses. Also, relative or absolute activity levels in the trichome cells can be compared to constitutive control promoters, such as the 35S promoter, double-35S promoter, or to other promoters which have activity in trichomes, such as the CYP71D16 promoter or OASA1 promoter. It is understood that preferably average promoter activity levels are determined and compared using statistical methods.

Thus, whether activity is found in trichome cells at a certain time (spatio-temporal activity) can, for example, be tested by transforming plants or plant cells with a promoter-reporter gene construct and analyzing trichomes during various developmental stages for the RNA transcript or reporter protein (or its activity). One simple test employs for example histochemical GUS staining, whereby visual assessment of blue colour indicates activity in trichomes and at various developmental stages of the trichomes.

As already mentioned, it is preferred that the promoter activity is constitutive and preferably also strong in trichome cells, especially in the host species or variety into which the sequence is introduced. Constitutive activity means that the transcript of any nucleic acid sequence operably linked to the promoter is preferably produced in trichome cells under most (normal, non-stressed) physiological and developmental conditions. In one embodiment, the promoters according to the invention are preferably not active in epidermal cells. Preferably the promoters are active in all glandular trichomes found on stems, flowers and/or (young) leaves.

Preferably, the promoters according to the invention provide strong, constitutive activity in trichomes of all plant species, both dicotyledonous species and monocotyledonous species, such as described below (e.g. tomato, tobacco, *Brassica*, melon and lettuce and others).

The strength (quantitative activity) of the promoters according to the invention (including fragments or variants) in terms of its ability to drive expression of nucleic acid sequences linked downstream (3') can be determined quantitatively using various known methods. For example, the amount of transcribed transcript (mRNA) can be quantified using quantitative RT-PCR or northern blotting. Preferably, the promoter strength is at least essentially equal to the activity in the trichomes of the CaMV 35S (Franck et al., supra) under normal (non-stressed) conditions. "Strong" means, thus, that the promoter strength is preferably at least about identical, but more preferably stronger than that of 35S in trichomes under normal, non-stressed conditions. Most preferably, the average quantitative promoter activity in the trichomes is at least equivalent to the activity of the CaMV 35S promoter, or is at least 5%, 10%, 20%, 30%, 35%, 40%, 45%, 50%, 55%, 60%, 70%, 75%, or more, higher than the average activity of the CaMV 35S promoter in trichomes. It is understood that the same copy number and zygosity level of transformants should be compared, e.g. hemizygous or homozygous for the transgene. Preferably, single copy transformants are identified and compared. The strength of the 35S promoter in the trichomes of a host plant can be tested by analyzing and preferably quantifying e.g. GUS gene expression in a P35S-GUS plant and comparing this to the expression of the promoters according to the invention.

Alternatively, "strong" may mean that the promoter strength is preferably at least about identical, but more preferably stronger than that of at least one of the promoters consisting of SEQ ID NO: 1, 2 or 3 in trichomes under normal, non-stressed conditions. Most preferably, the average quantitative promoter activity in the trichomes is at least equivalent to the activity of at least one of the promoters consisting of SEQ ID NO: 1, 2 or 3, or is at least 5%, 10%, 20%, 30%, 35%, 40%, 45%, 50%, 55%, 60%, 70%, 75%, or more, higher than the average activity of at least one of the promoters consisting of SEQ ID NO: 1, 2 or 3 in trichomes. It is understood that the same copy number and zygosity level of transformants should be compared, e.g. hemizygous or homozygous for the transgene. Preferably, single copy transformants are identified and compared.

Thus, the strength of the promoters according to the invention preferably remains essentially unchanged, or is at least not reduced (or not significantly reduced), when the plant tissues or organs or plants comprising the promoter are exposed to stress conditions, selected at least from one or preferably several of: drought stress, heat stress, water-stress (both too much and too little water), pathogen stress (e.g. virus infection such as CMV, fungal infection, bacterial infection, etc.), pest stress (e.g. insect feeding), wounding, salt stress, radiation stress, etc. Again, quantitative tests can be used to determine this. For example, recombinant plants comprising the promoter may be transferred from a normal temperature environment to a warm environment (such as about 27° C. to up to about 50° C.), and the promoter activity in various tissues may be compared to the activity in the same tissues under the normal and under the warm temperature conditions.

In one embodiment the use of any of the above promoters for the expression of homologous or heterologous nucleic acid sequences in a recombinant cell or organism, especially a plant cell or plant, is provided. This use comprises operably linking the promoter to a homologous or heterologous nucleic acid sequence and transforming a plant or plant cell, as described further below.

Although the focus above is on the use of the promoters according to the invention in plants and plant cells, it is also an embodiment of the invention to use the promoters for the expression of homologous or heterologous nucleic acid sequences in other cells and organisms, such as in any prokaryotic or eukaryotic cells or organisms, e.g. bacteria, fungi (including yeasts, such as *Pichia, Hansenula*, etc.), mammals, human cells or cell lines, etc.

Chimeric Genes and Vectors According to the Invention

In one embodiment of the invention any of the above nucleic acid sequences having promoter activity, are used to make chimeric genes, and vectors comprising these for transfer of the chimeric gene into a host cell and expression of an operably linked homologous or heterologous nucleic acid sequence in host cells, such as cells, tissues, organs or whole organisms derived from transformed cell(s).

Host cells are preferably plant cells. Any plant may be a suitable host, such as monocotyledonous plants or dicotyledonous plants, for example maize/corn (*Zea* species, e.g. *Z. mays, Z. diploperennis* (chapule), *Zea luxurians* (Guatemalan teosinte), *Zea mays* subsp. *huehuetenangensis* (San Antonio Huista teosinte), *Z. mays* subsp. *mexicana* (Mexican teosinte), *Z. mays* subsp. *parviglumis* (Balsas teosinte), *Z. perennis* (perennial teosinte) and *Z. ramosa*, wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc.), sunflower (*Helianthus annus*), tobacco (*Nicotiana species*), alfalfa (*Medicago sativa*), rice (*Oryza* species, e.g. *O. sativa* indica cultivar-group or *japonica* cultivar-group), forage grasses, pearl millet (*Pennisetum* species. e.g. *P. glaucum*), tree species, vegetable species, such as *Lycopersicon* ssp (recently reclassified as belonging to the genus *Solanum*), e.g. tomato (*L. esculentum*, syn. *Solanum lycopersicum*) such as e.g. cherry tomato, var. *cerasiforme* or current tomato, var. *pimpinellifolium*) or tree tomato (*S. betaceum*, syn. *Cyphomandra betaceae*), potato (*Solanum tuberosum*) and other *Solanum* species, such as eggplant (*Solanum melongena*), pepino (*S. muricatum*), cocona (*S. sessiliflorum*) and naranjilla (*S. quitoense*); peppers (*Capsicum annuum, Capsicum frutescens*), pea (e.g. *Pisum sativum*), bean (e.g. *Phaseolus* species), carrot (*Daucus carona*), *Lactuca* species (such as *Lactuca sativa, Lactuca indica, Lactuca perennis*), cucumber (*Cucumis sativus*), melon (*Cucumis melo*), zucchini (*Cucurbita pepo*), squash (*Cucurbita maxima, Cucurbita pepo, Cucurbita mixta*), pumpkin (*Cucurbita pepo*), watermelon (*Citrullus lanatus* syn. *Citrullus vulgaris*), fleshy fruit species (grapes, peaches, plums, strawberry, mango, melon), ornamental species (e.g. Rose, *Petunia, Chrysanthemum*, Lily, Tulip, *Gerbera* species), woody trees (e.g. species of *Populus, Salix, Quercus, Eucalyptus*), fibre species e.g. flax (*Linum usitatissimum*) and hemp (*Cannabis sativa*). In one embodiment vegetable species, especially *Solanum* species (including *Lycopersicon* species) are preferred.

Thus, for example species of the following genera may be transformed: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Cucumis, Hyoscyamus, Lycopersicon, Solanum, Nicotiana, Malus, Petunia, Digitalis, Majorana, Ciahorium, Helianthus, Lactuca, Bromus, Citrullus, Asparagus, Antirrhinum, Heterocallis, Nemesis, Pelargonium, Panieum, Pennisetum, Ranunculus, Senecio, Salpiglossis, Browaalia, Glycine, Pisum, Phaseolus, Gossypium, Glycine, Lolium, Festuca, Agrostis*. A further preference is for each of *Cucurbita, Brassica, Lycopersicon, Solanum, Oryza* and *Zea*. A preference is for each of *Avena, Medicago, Capsicum, Nicotiana, Lactuca, Pisum, Cucumis, Cucurbita, Brassica, Solanum* (including *Lycopersicon*), *Oryza* and *Zea*.

The construction of chimeric genes, and vectors for introduction of chimeric genes into the genome of host cells, is generally known in the art. To generate a chimeric gene the trichome specific promoter sequence is operably linked to another nucleic acid sequence which is to be transcribed in the host cells, using standard molecular biology techniques. The promoter sequence may already be present in a vector so that the nucleic acid sequence which is to be transcribed is simply inserted into the vector downstream of the promoter sequence. The vector is then used to transform the host cells and the chimeric gene is preferably inserted in the nuclear genome or into the plastid, mitochondrial or chloroplast genome, so that the downstream nucleic acid sequence is expressed due to the activity of the promoter (e. g., Mc Bride et al., 1995 Bio/Technology 13, 362; U.S. Pat. No. 5,693, 507).

A chimeric gene, therefore, preferably comprises an trichome specific promoter as described above, operably linked to a homologous or heterologous nucleic acid sequence, and optionally followed by a 3' nontranslated nucleic acid sequence (3'UTR). The homologous or heterologous nucleic acid sequence may be a sequence encoding a protein or peptide, or it may be a sequence which is transcribed into an active RNA molecule, such as an sense and/or antisense RNA (sense and antisense RNA includes for example dsRNA or stem-loop RNA structures) suitable for silencing a gene or gene family in the host cell or organism.

The trichome specific promoter-comprising chimeric gene can be stably inserted in a conventional manner into the nuclear genome of a single plant cell, and the so-transformed plant cell can be used in a conventional manner to produce a transformed plant that has an altered phenotype due to the expression of the chimeric gene.

In this regard, a T-DNA vector, comprising a trichome specific promoter (or variant or fragment as described above) operably linked to a further nucleic acid sequence, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Preferred T-DNA vectors each contain a trichome specific promoter operably linked to the nucleic acid sequence to be transcribed between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247, or particle or microprojectile bombardment as described in US 2005/055740 and WO 2004/092345), pollen mediated transformation (as described, for example in EP 0 270 356 and WO 85/01856), protoplast transformation as, for example, described in U.S. Pat. No. 4,684,611, plant virus-mediated transformation, liposome-mediated transformation (as described, for example in U.S. Pat. No. 4,536,475), and other methods such as those described methods for transforming certain lines of maize (e. g., U.S. Pat. No. 6,140,553; Fromm et al., 1990, Bio/Technology 8, 833-839; Gordon-Kamm et al., 1990, The Plant Cell 2, 603-618) and rice (Shimamoto et al., 1989, Nature 338, 274-276; Datta et al. 1990, Bio/Technology 8, 736-740) and the method for transforming monocots generally (WO 92/09696). For cotton transformation see also WO 00/71733, and for rice transformation see also the methods described in WO 92/09696, WO 94/00977 and WO 95/06722. For *sorghum* transformation see e.g. Jeoung J M et al. 2002, Hereditas 137: 20-8 or Zhao Z Y et al. 2000, Plant Mol Biol. 44:789-98). For tomato or tobacco transformation see also An G. et al., 1986, Plant Physiol. 81: 301-305; Horsch R. B. et al., 1988, In: Plant Molecular Biology Manual A5, Dordrecht, Netherlands, Kluwer Academic Publishers. pp 1-9; Koornneef M. et al., 1986, In: Nevins D. J. and R. A. Jones, eds. Tomato Biotechnology, New York, N.Y., USA, Alan R. Liss, Inc. pp 169-178). Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably the chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

The resulting transformed plant can be used in a conventional plant breeding scheme to produce more transformed plants containing the transgene. Single copy transformants can be selected, using e.g. Southern Blot analysis or PCR based methods or the Invader® Technology assay (Third Wave Technologies, Inc.). Transformed cells and plants can easily be distinguished from non-transformed ones by the presence of the chimeric gene. The sequences of the plant DNA flanking the insertion site of the transgene can also be sequenced, whereby an "Event specific" detection method can be developed, for routine use. See for example WO 01/41558, which describes elite event detection kits (such as PCR detection kits) based for example on the integrated sequence and the flanking (genomic) sequence.

In one embodiment the nucleic acid sequence which is to be transcribed, and optionally translated (if it is a coding sequence), is inserted into the plant genome so that the sequence to be transcribed is upstream (i.e. 5') of suitable 3'end transcription regulation signals ("3' end") (i.e. transcript formation and polyadenylation signals). Polyadenylation and transcript formation signals include those of the nopaline synthase gene ("3' nos") (Depicker et al., 1982 J. Molec. Appl. Genetics 1, 561-573.), the octopine synthase gene ("3'ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others.

In one embodiment the 3'end sequence used is that of a monoterpene synthase 1 (linalool synthase), sesquiterpene synthase 1 or methyl-ketone synthase, such as the 3'end of the gene of SEQ ID NO: 1, 2, or 3 or a variant thereof.

The nucleic acid sequence to be expressed is in one embodiment a sequence encoding a protein or peptide, including hybrid proteins or peptides or fusion proteins. The coding sequence may be of any origin, i.e. plant, fungus (including yeast), animal, bacterial, synthetic, viral, human, etc. It may also comprise a sequence encoding a targeting peptide, such as a secretion signal peptide or a plastid targeting signal. A coding sequence may also be linked in-frame to a gene encoding a selectable or scorable marker, such as for example the neo (or nptII) gene (EP 0 242 236) conferring kanamycin resistance, so that the cell expresses a fusion protein which is easily detectable. Although the coding region (cDNA or genomic DNA) of any gene may be used, examples of the coding regions of the following genes are preferably operably linked to a promoter according to the invention:

1. pest or pathogen disease signal transduction pathway genes or pathways, or disease resistance genes or pathways; for example antifungal or antiviral proteins, insecticidal proteins, and the like.
2. herbivore repellent genes or pathways
3. pest, pathogen or herbivore attractant genes or pathways (to generate catch or trap crops)
4. secondary metabolite biosynthesis genes or pathways, including genes for the production of therapeutic and/or pharmacologically and cosmetically important products or industrially valuable compounds, genes providing nutritional or nutraceutical compounds, flavourants or scents, aromas (herbs), pollinator attractor genes
5. phytoremediation applications e.g. ion and pollutant metal secretion genes (Psaras et al., 2000, Ann Bot 86, 73)

The chimeric genes or vectors according to the invention can also be used to transform microorganisms, such as bacteria (e.g. *Escherichia coli, Pseudomonas, Agrobacterium, Bacillus*, etc.) or fungi or algae or insects, or the genes or vectors may be used to engineer viruses. Transformation of bacteria with nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205) and WO 90/06999. For expression of coding sequences in prokaryotic host cell, the codon usage of the nucleic acid sequence may be optimized accordingly (likewise, for expression of coding sequences in plant cells, codon usage of the nucleic acid sequence may be optimized as known). Intron sequences should be removed and other adaptations for optimal expression may be made as known.

For obtaining enhanced expression of a nucleic acid sequence in monocot plants such as grass species, e.g. maize or rice, an intron, preferably a monocot intron, can be added to the chimeric gene. For example the insertion of the intron of the maize Adh1 gene into the 5' regulatory region has been shown to enhance expression in maize (Callis et. al., 1987, Genes Develop. 1: 1183). Likewise, the HSP70 intron, as described in U.S. Pat. No. 5,859,347, may be used to enhance expression. Thus, one or more introns may optionally be inserted into any of the promoter sequences according to the invention, or into the 5' UTR or the coding sequence.

Encompassed herein are also transgenic plants (and parts thereof) comprising trichome specific promoter, operably linked to a protein or polypeptide encoding nucleic acid sequence, as described further below.

In a different embodiment the promoters according to the invention are used to make a chimeric gene and vector for gene silencing, whereby the promoter is operably linked to a sense and/or antisense nucleic acid sequence of a target gene (endogenous gene or gene family which is to be silenced specifically in trichome cells).

"Gene silencing" refers to the down-regulation or complete inhibition of gene expression of one or more target genes. The use of inhibitory RNA to reduce or abolish gene expression is well established in the art and is the subject of several reviews (e.g. Baulcombe, 1996, Plant Cell 8: 1833-1844; Stam et al., 1997, Plant Journal 12: 63-82; Depicker and Van Montagu, 1997, Curr. Opinion Cell Biol. 9: 373-382). There are a number of technologies available to achieve gene silencing in plants, such as chimeric genes which produce antisense RNA of all or part of the target gene (see e.g. EP 0 140 308 B1, EP 0 240 208 B1 and EP 0 223 399 B1), or which produce sense RNA (also referred to as co-suppression), see EP 0 465 572 B1.

The most successful approach so far has however been the production of both sense and antisense RNA of the target gene ("inverted repeats"), which forms double stranded RNA (dsRNA) in the cell and silences the target gene(s). Methods and vectors for dsRNA production and gene silencing have been described in EP 1 068 311, EP 983 370 A1, EP 1 042 462 A1, EP 1 071 762 A1 and EP 1 080 208 A1.

A vector according to the invention may therefore comprise a trichome specific promoter operably linked to a sense and/or antisense DNA fragment of a target gene. Short (sense and antisense) stretches of the target gene sequence, such as at least about 17, 18, 19, 20, 21, 22, 23, 24 or 25 nucleotides of coding or non-coding sequence may be sufficient. Longer sequences are frequently also used, such as at least about 100, 200, 250, 300, 400, 500, 1000, 1500 nucleotides, or more. Preferably, the sense and antisense fragments are separated by a spacer sequence, such as an intron, which forms a loop (or hairpin) upon dsRNA formation. Any stretch of the target gene may be used to make a gene silencing vector and a transgenic plant in which the target gene or gene family is silenced. A convenient way of generating hairpin constructs is to use generic vectors such as pHANNIBAL and pHELLSGATE, vectors based on the Gateway® technology (see Wesley et al. 2004, Methods Mol Biol. 265:117-30; Wesley et al. 2003, Methods Mol Biol. 236:273-86 and Helliwell & Waterhouse 2003, Methods 30(4):289-95.), all incorporated herein by reference.

By choosing conserved nucleic acid sequences of the target gene, the family members in a host plant can be silenced in trichome cells.

Encompassed herein are also transgenic plants comprising trichome specific promoter, operably linked to a sense and/or antisense DNA fragment of a target gene nucleic acid sequence and exhibiting a target gene silencing phenotype. The phenotype will depend on the function of the gene, and may be a chemical or molecular change, macroscopically visible or not visible. Such chimeric genes and vectors can, therefore, also be used to determine or verify the function of genes in trichomes.

The chimeric genes according to the invention may be introduced stably into the host genome or may be present as an episomal unit.

Transgenic Cells and Organisms According to the Invention

Transgenic cells and organisms, especially plants, plant cells, tissues or organs are provided, obtainable by the above methods. These cells and organisms are characterized by the presence of a chimeric gene in their cells or genome by the presence of a promoter according to the invention. In addition, the mRNA transcript or the translated protein, may alter the phenotype of the cells or organism, e.g. of the plant trichomes, especially the glandular trichomes.

In one embodiment the chimeric gene introduced into the plant is composed of parts which all occur naturally in the host genus or species, e.g. if a host plant of the genus *Solanum* is to be transformed, preferably the promoter according to the invention from the genus *Solanum* is used and operably linked to a nucleic acid sequence also from the genus *Solanum* and optionally a 3'UTR from the genus *Solanum*. The same can be applied to the species of the host. Although the plant will carry a transgene, all nucleotide elements thereof are naturally found in the host genus or species (albeit not in this combination), reducing regulatory problems and improving public acceptance.

The position of the chimeric gene in the genome can affect the activity of the promoter and the expression level of the chimeric gene. Therefore, transformants ("Events" or "Transformation Events") expressing high, constitutive levels of the protein or of the sense and/or antisense transcript (when silencing constructs are used) can be selected by e.g. analysing copy number (Southern blot analysis), mRNA transcript levels (e.g. Northern blot analysis or RT-PCR) or by analysing the presence and level of protein encoded by the nucleic acid sequence (e.g. SDS-PAGE followed by Western blot analysis; ELISA assays, immunocytological assays, etc). The transformants can also be tested for the stability of expression under one or more biotic and/or abiotic stress conditions and those events which retain high, constitutive expression under one or more of the desired conditions can be identified and selected for further use.

The transgenic plants can be used in traditional breeding methods, such as crossing, selfing, backcrossing, etc. By selfing the transformants, plants which are homozygous for the transgene can be generated. Breeding procedures are known in the art and are described in standard text books of plant breeding, e.g., Allard, R. W., Principles of Plant Breeding (1960) New York, N.Y., Wiley, pp 485; Simmonds, N. W., Principles of Crop Improvement (1979), London, UK, Longman, pp 408; Sneep, J. et al., (1979) Tomato Breeding (p. 135-171) in: Breeding of Vegetable Crops, Mark J. Basset (1986, editor), The Tomato crop: a scientific basis for improvement, by Atherton, J. G. & J. Rudich (editors), Plant Breeding Perspectives (1986); Fehr, Principles of Cultivar Development—Theory and Technique (1987) New York, N.Y., MacMillan.

Transgenic cells or organisms can also be used in cell cultures (plant cell cultures, bacterial or fungal cell cultures such as yeast cultures, human or mammalian cell cultures, insect cell cultures), for example for the large scale production of recombinant proteins. In one embodiment a cell culture is provided, comprising cells comprising a promoter according to the invention.

Methods and Uses According to the Invention

Also provided is a method for making a transgenic plant or plant cell, comprising the steps of:
 (a) generating a chimeric gene or a vector comprising a promoter according to the invention, operably linked to a nucleic acid sequence to be expressed;
 (b) transforming a plant or plant cell with said chimeric gene or vector; and, optionally,
 (c) regenerating a transgenic plant or plants.

The regenerated plant (or progeny thereof which retain the transgene) or parts thereof may be used for various purposes, such as in agriculture as such or for molecular farming. The further use depends on the phenotype conferred by the transgene. For example, if the transgenic plant produces high levels of a secondary metabolite in the trichomes, the plants will be grown and the metabolite harvested. Thus, all or part of the plants may be harvested for either human or animal consumption or for industrial purposes, depending on the transgene. Also, different parts of the plant may be harvested for different purposes, e.g. the fruit or seed may be harvested for consumption, while the leaves, stems and/or flowers may be harvested for industrial purposes.

Obviously, the phenotype conferred by the transgene can be tested, e.g. in field trials (e.g. disease or pest resistance tests can be carried out using conventional methods).

Transgenic plants may be identified which provide strong (e.g. constitutive) promoter activity in trichomes under non-stress conditions, and whereby the promoter activity remains essentially unchanged (is at least not reduced, or not reduced significantly) when the plant is exposed to one or more biotic and/or abiotic stresses.

The plants may be used in conventional agricultural and breeding methods.

FIGURES

Figure 2:
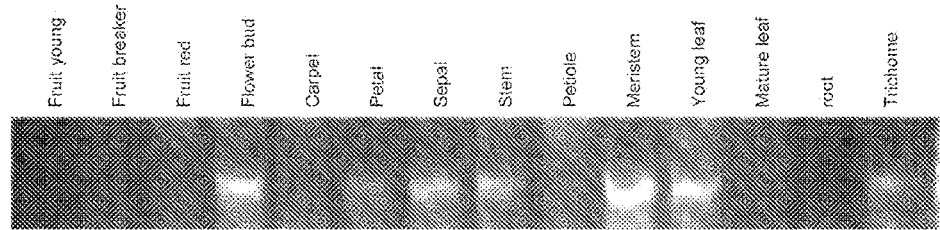
Figure 4A:
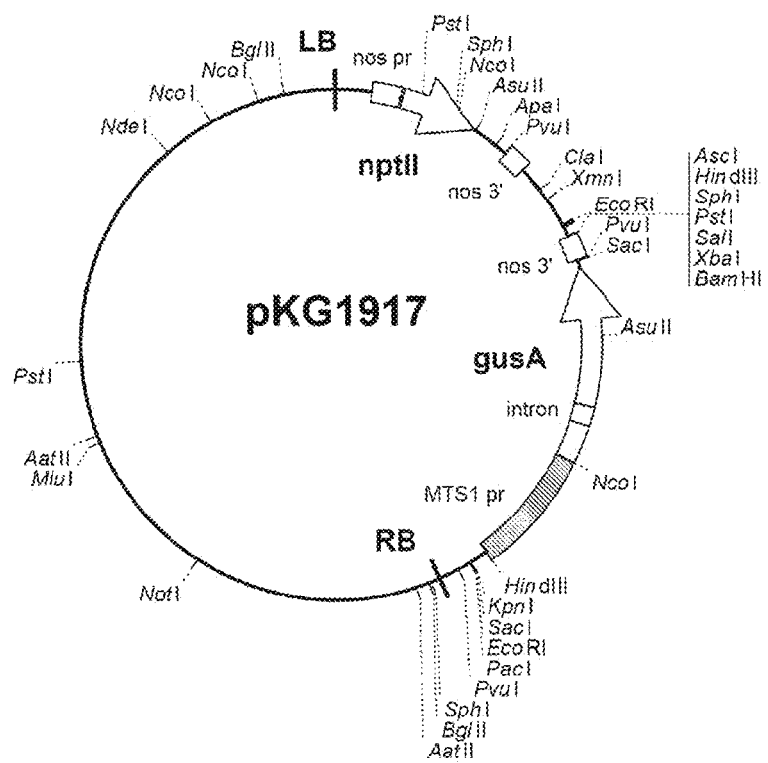
Figure 4B:
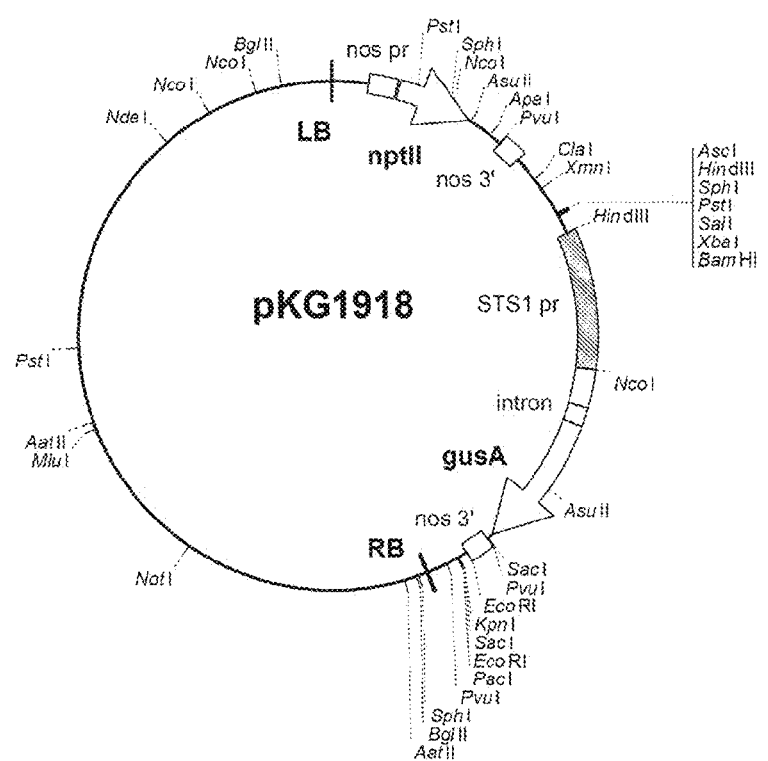
Figure 5:
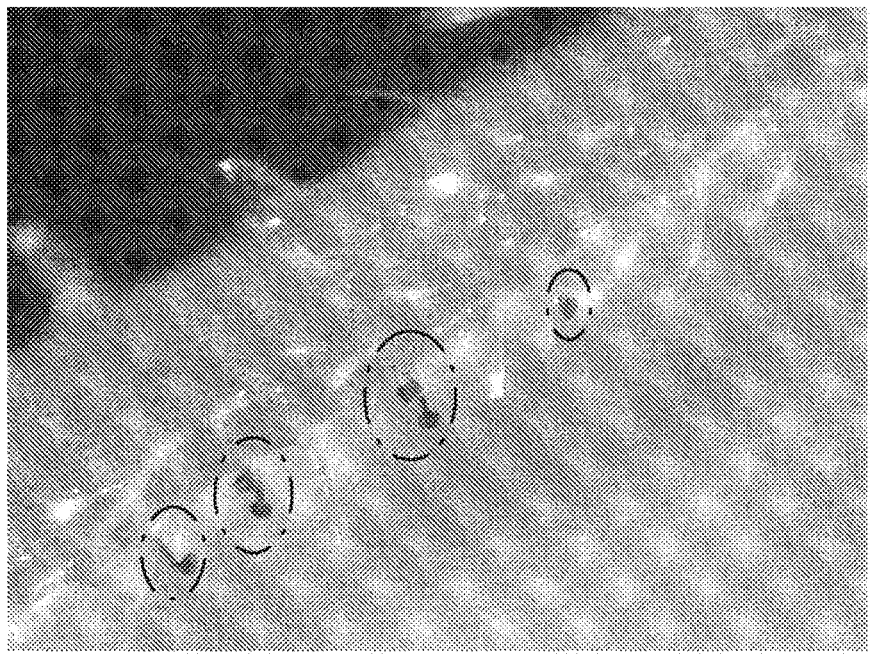

FIG. 1.
ShSTS1 expression in tomato (*S. habrochaites* LA1777) leaf with trichomes (LT), stem with trichomes (ST) bald stem (BS) and trichomes (T).
FIG. 2.
SlSTS1 expression in different organs of *S. lycopersicum* (Moneymaker)
FIG. 3
Vector map of pKG1662
FIGS. 4A and 4B
Vector maps of (A) pKG1917; and (B) pKG1918.
FIG. 5
Photograph of a SlMTS1p:GUS transformed tomato plant showing blue Xgluc-staining of glandular trichomes (encircled).

The following non-limiting Examples describe the use of promoters according to the invention. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

EXAMPLES

Selection of Gene for Promoter Isolation cDNA of *S. lycopersicum* cv Moneymaker and the wild tomato *S. habrochaites* var LA1777 was isolated. Tissue specific expression levels of *S. lycopersicum* Monoterpene Synthase 1 (SlMTS1; AY840091), *S. lycopersicum* Sesquiterpene Synthase 1 (SlSTS1; AF279453), *S. habrochaites* Sesquiterpene Synthase 1 (ShSTS1; AF279455) were tested in several different plant organs including trichomes and bald stem (from which trichomes were removed). Expression of the ShSTS1 gene is absent in the absence of trichomes (FIG. 1). Sesquiterpene synthase 1 expression (STS1) was confirmed in various plant organs (FIG. 2). SlSTS1 transcripts were detected in the tissues containing trichomes, e.g. flower meristems and young leaf. Expression is absent in the fruit and root tissues.

Promoter Sequence Isolation

To obtain promoter sequences a chromosome walk on genomic DNA was performed. Total genomic DNA was isolated from *S. lycopersicum* (Moneymaker) and *S. habrochaites* (LA1777). Two µg of gDNA was digested separately with several 6-base recognition blunt cutting restriction enzymes (SmaI, HinCII, EcoRV, PmiI, DraI, PvuII, SspI, ScaI), extracted with phenol:chloroform:isoamylalcohol and precipitated in ethanol according to standard procedures. Ten μl of long strand adaptor (100 μM) was mixed with 10 μl short strand adaptor (100 μM) after which the adaptor strands were annealed by heating to 95° C. for 2 minutes followed by a slow cooling to room temperature. An excess of adaptor was ligated overnight to the genomic DNA fragments at 4° C.

Based on the 5' sequence information of nucleic acid sequences AY840091, AF279453 and AF279455 specific reverse primers were designed.

| Primer name | 5' - 3' sequence | SEQ ID NO: |
|---|---|---|
| adapter long strand | CTAATACGACTCACTATAGGACTCGAG CGGCCGCCCGGGCAGGT | 4 |
| adapter short strand | ACCTGCCCGGGC | 5 |
| adapter primer | CTAATACGACTCACTATAGGGC | 6 |
| nested adapter primer | TCGAGCGGCCGCCCGGGCAGGT | 7 |
| ShSTS1 promoter (8) | CCCCAAACAGTTGGGTGAAAATTAGCC | 8 |
| ShSTS1 nested (9) | GGACGAGACTTATTAGCAGAAGAAGCAGCC | 9 |
| SlSTS1 promoter (43) | TTCATGAGTATAAGAAAGGAAATGATATCC | 10 |
| SlSTS1 nested (44) | GGAAATGATATCCCCAAACAGATGGGTG | 11 |
| SlMTS1 promoter (54) | GGTAAATAATGATGGTCTCTTGAAGG | 12 |
| SlMTS1 nested (55) | GACCACCATCATCCCTATGTTACTC | 13 |

A nested PCR on the different genomic DNA fragments with adaptor and specific primers resulted in novel promoter sequence fragments. Cloning of PCR products was performed with the Original TA Cloning® Kit from Invitrogen BV using plasmid pCR@2.1. After sequencing new reverse primers could be designed on the novel promoter fragment sequence. A PCR on genomic DNA with primers containing appropriate restriction sites for cloning resulted in the final DNA regulatory nucleic acid fragments.

These are shown in SEQ ID NO: 1, 2, 3.
Promoter Sequences
SEQ ID NO 1: '1.5 kb (1426 bp) ShSTS1 promoter
SEQ ID NO 2: '1.9 kb (1907 bp) SlSTS1 promoter
SEQ ID NO 3: '1.2 kb (1253 bp) SlMTS1 promoter

| Primer name | 5' - 3' sequence | SEQ ID NO: |
|---|---|---|
| ShSTS1 full forward | CCCTCGAGTATCTATAGACCATATC | 14 |
| ShSTS1 full reverse | GCAGAAGAAGCAGCCATGGCTTGTTC | 15 |
| SlSTS1 full forward | TTAATTAAGCATATATATATATATCATAACTAGTAG | 16 |
| SlSTS1 full reverse | GCGGCCGCTGCTTGTTTGCTTTTTTTCAAGC | 17 |
| SlMTS1 full forward | GCGGCCGCGTTTCATTCAAAGTAGTGGTGTC | 18 |
| SlMTS1 full reverse | CCATGGTTTATTTGTTCTGCTCAATTAC | 19 |

Transformation Constructs

Figure 3:
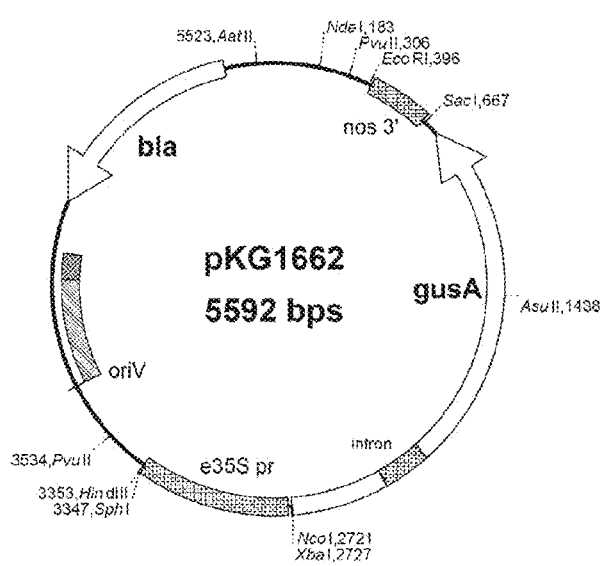

Final promoter sequences [SEQ ID NO: 1, 2 and 3] were placed in front of the GUS-A marker gene in the pKG1662 vector (FIG. 3). Promoter and marker gene were then shuttled into the multiple cloning site of the binary pBIN-plus vector (Van Engelen et al., 1995, Transgenic Res, 288). This construct was then incorporated into Agrobacterium tumefaciens var. GV3101 and used to transform tomato S. lycopersicum var. Moneymaker according to the method described by Koornneef et al. (1986. Transformation of tomato. In: Nevins D. J. and R. A. Jones, eds. Tomato Biotechnology. New York, N.Y., USA, Alan R. Liss, Inc. pp 169-178.). Constructs were transformed and regenerated under kanamycin selection and primary regenerants ($T_0$) were grown to seed.

As a control, a construct containing the CER6 promoter from Arabidopsis thaliana was transformed into tomato additionally. The CER6 promoter was shown to be highly effective in directing epidermis-specific expression in both A. thaliana and Nicotiana tabacum (Hooker et al., 2002 Plant Physiol 129, 1568). This epidermal promoter is also active in trichome tissue of N. tabacum.

Expression Analysis of Transformants

Quantitative and qualitative β-glucuronidase (GUS) activity analyses were performed on $T_1$ plants.

Qualitative analysis of promoter activity was carried out using histological GUS assays. Various plant parts were incubated overnight at 37° C. in the presence of atmospheric oxygen with Xgluc (5-Bromo-4-chloro-3-indolyl β-D-glucuronide cyclohexylamine salt) substrate in phosphate buffer (1 mg/ml, $K_2HPO_4$, 40 mM, $KH_2PO_4$, 10 mM, pH 7.2, 0.2% Triton X-100). The samples were de-stained by repeated washing with ethanol. Non-transgenic plants were used as negative controls. Thrichomes of transgenic plants with ShSST1p:GUS and SlMTS1:GUS showed bright blue trichomes whereas the non-trichome tissues of these transgenic plants and the trichomes of non-transgenic control plants were not colored.

Quantitative analysis of promoter activity are carried out using a fluorometric GUS assay. Total protein samples are prepared from young leaf material; samples are prepared from pooled leaf pieces of approximately the same size and developmental stage from different parts of each plant tested. Fresh leaf material are ground in phosphate buffer ($Na_2HPO_4$, 77.4 mM, $NaH_2PO_4$, 22.6 mM) using metal beads followed by centrifugation and collection of the supernatant.

The invention claimed is:

1. A transgenic plant, plant cell, plant tissue or plant organ comprising a chimeric gene integrated in its genome, which chimeric gene comprises a constitutive promoter operably linked to a homologous or heterologous nucleic acid sequence, wherein the promoter is selected from the group consisting of the nucleic acid sequence of SEQ ID NO: 1, SEQ ID NO: 2 and SEQ ID NO: 3.

2. The plant, cell, tissue or organ according to claim 1, wherein the promoter is specifically active in trichomes.

3. The plant, cell, tissue or organ according to claim 1, wherein the plant is a member of the family Solanaceae.

4. An isolated nucleic acid sequence comprising a chimeric gene containing trichome-specific promoter activity when introduced into plant cells, which nucleic acid sequence comprises a first nucleic acid sequence selected from the group consisting of SEQ ID NO: 1, SEQ ID NO:2 and SEQ ID NO:3, and a second nucleic acid sequence not associated in nature with said first nucleic acid sequence.

5. The isolated nucleic acid sequence according to claim 4, where said chimeric gene comprises a homologous or heterologous nucleic acid.

6. A vector comprising a nucleic acid sequence according to claim 4.

7. A transgenic plant or plant cell comprising the isolated nucleic acid sequence according to claim 5.

8. A method for making a transgenic plant or plant cell, comprising the steps of:

(a) generating an isolated nucleic acid sequence according to claim 5;
(b) transforming a plant cell with said isolated nucleic acid sequence; and,
(c) obtaining said transgenic plant or plant cell.

9. The plant, cell, tissue or organ according to claim 2 wherein the promoter is active only in glandular trichomes.

10. A transgenic plant or plant cell comprising the vector according to claim 6.

11. A method for making a transgenic plant or plant cell, comprising the steps of:
(a) generating a vector according to claim 6;
(b) transforming a plant or plant cell with said vector; and,
(c) optionally, regenerating transgenic plants from said cell.

12. The isolated nucleic acid sequence according to claim 4, wherein said chimeric gene comprises a 3' UTR sequence.

13. The method according to claim 11, wherein a transgenic plant is regenerated from said transgenic plant cell.

\* \* \* \* \*